United States Patent
Koseoglu et al.

(10) Patent No.: US 10,781,168 B2
(45) Date of Patent: Sep. 22, 2020

(54) OXIDIZED DISULFIDE OIL SOLVENT COMPOSITIONS

(71) Applicant: Saudi Arabian Oil Company, Dhahran (SA)

(72) Inventors: Omer Refa Koseoglu, Dhahran (SA); Robert Peter Hodgkins, Dhahran (SA); Adnan Al-Hajji, Dhahran (SA); Hendrik Muller, Dhahran (SA); Nadrah Al-Awani, Dhahran (SA); Frederick Marie Adam, Dhahran (SA); Qasim Saleem, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/210,266

(22) Filed: Dec. 5, 2018

(65) Prior Publication Data

US 2020/0181074 A1 Jun. 11, 2020

(51) Int. Cl.
| | |
|---|---|
| *C07C 317/04* | (2006.01) |
| *C07C 315/02* | (2006.01) |
| *C10G 53/14* | (2006.01) |
| *C07C 7/10* | (2006.01) |
| *C07C 319/30* | (2006.01) |
| *C10G 27/10* | (2006.01) |

(52) U.S. Cl.
CPC .......... *C07C 317/04* (2013.01); *C07C 315/02* (2013.01); *C10G 53/14* (2013.01); *C07C 7/10* (2013.01); *C07C 319/30* (2013.01); *C10G 27/10* (2013.01)

(58) Field of Classification Search
CPC ... C07C 317/04; C07C 315/02; C07C 319/30; C07C 7/10; C10G 53/14; C10G 27/10
See application file for complete search history.

(56) References Cited

U.S. PATENT DOCUMENTS

| | | | | | |
|---|---|---|---|---|---|
| 2,433,395 | A | * | 12/1947 | Shoemaker | B01J 27/00 562/118 |
| 4,729,835 | A | * | 3/1988 | McNeillie | C02F 1/722 210/759 |
| 4,992,578 | A | * | 2/1991 | Husain | C07C 381/04 560/307 |

FOREIGN PATENT DOCUMENTS

WO 2015085522 A1 6/2015

OTHER PUBLICATIONS

Engel et al. (Remove mercaptans from hydrocarbon condensates and NGL streams, pp. 1-6, published Feb. 2016) (Year: 2016).*
Cantau et al., Oxidation of nauseous sulfur compounds by photocatalysis or photosensitization, Catalysis Today, vol. 122, 2007, 12 pages.

* cited by examiner

*Primary Examiner* — Yevgeny Valenrod
*Assistant Examiner* — Blaine G Doletski
(74) *Attorney, Agent, or Firm* — Abelman, Frayne & Schwab (57) ABSTRACT

Oxidized disulfide oil (ODSO) solvent compositions are derived from by-product disulfide oil (DSO) compounds produced as by-products from the generalized mercaptan oxidation (MEROX) processing of a refinery feedstock. The oxidized disulfide oil (ODSO) solvent compositions comprise at least a primary oxidized disulfide oil (ODSO) compound selected from either water soluble or water insoluble oxidized disulfide oil (ODSO) compounds and in some embodiments at least 0.1 ppmw of a secondary oxidized disulfide oil (ODSO) compound that is a water soluble oxidized disulfide oil (ODSO) compound.

14 Claims, 5 Drawing Sheets

OXIDIZED DISULFIDE OIL SOLVENT COMPOSITIONS

BACKGROUND OF THE INVENTION

Field of the Invention

This invention relates to solvent compositions.

Description of Related Art

A solvent is a compound or composition that can dissolve a solute to produce a solution. A solvent is usually a liquid, but can be a solid, gas, or supercritical fluid. Solvents have various applications in the chemical, pharmaceutical, oil and gas industries, and are commonly used in chemical syntheses and purification processes. The amount of solute that can be dissolved in a certain volume of solvent generally varies with temperature.

Common uses for organic solvents are in dry cleaning (e.g., tetrachloroethylene), as paint thinners (e.g., toluene, turpentine), as nail polish removers and adhesive compounds (e.g., acetone, methyl acetate, ethyl acetate), in spot removers (e.g., hexane, petrol ether), in detergents (e.g., citrus terpenes) and in perfumes (e.g., ethanol). Water, a polar molecule, is a solvent for other polar molecules and is the most common solvent used by living things. For example, all of the ions and proteins in a cell are dissolved in water contained in the cell.

Solvents can be classified into two broad categories: polar and non-polar. Generally, the dielectric constant of the solvent provides an appropriate measure of a solvent's polarity. The strong polarity of water is indicated by its high dielectric constant of 88 at 0° C. Solvents with a dielectric constant of less than 15 are generally considered to be non-polar. The dielectric constant measures the solvent's tendency to partly cancel the field strength of the electric field of a charged particle immersed in it. This reduction is then compared to the field strength of the charged particle in a vacuum. The dielectric constant of a solvent can be thought of as its ability to reduce the solute's effective internal charge. Generally, the dielectric constant of a solvent is an acceptable predictor of the solvent's ability to dissolve common ionic compounds, such as salts. It should be noted that the solubility of a solute is a function of the quantity of the solvent that can be dissolved in a specific volume of solvent at a specified temperature.

The dielectric constant of a solvent is only one measure of the polarity of the solvent, and other more specific measures of polarity exist that are sensitive to chemical structure. For example, the "Grunwald-Winstein mY scale" measures polarity in terms of solvent influence on the buildup of the positive charge of a solute during a chemical reaction, as described in Grunwald, E.; Winstein, S. "The Correlation of Solvolysis Rates". J. Am. Chem. Soc. 70 (2): 846, 1948, which is incorporated by reference.

The "Kosower's Z scale" measures polarity in terms of the influence of the solvent on UV-absorption maxima of a salt, usually pyridinium iodide, or the pyridinium zwitterion, as described in E. M. Kosower, J. Am. Chem. Soc., 80, 3253, 1958, "The Effect of Solvent on Spectra. I. A New Empirical Measure of Solvent Polarity: Z-Values", which is incorporated by reference.

The "donor number and donor acceptor scale" measures polarity in terms of how a solvent interacts with specific substances, e.g., a strong Lewis acid or a strong Lewis base, and is described in Gutmann, V., "The Donor-Acceptor Approach to Molecular Interactions", Plenum Press, New York and London, 1978, which is incorporated by reference.

The "Hildebrand parameter" is the square root of the cohesive energy density of the solvent system, as described in Hansen, C. M., Journal of Paint Technology, Vol. 39, No. 505, February 1967, "The Three Dimensional Solubility Parameter—Key to Paint Component Affinities I.—Solvents, Plasticizers, Polymers, and Resins", which is incorporated by reference. The cohesive energy density is the amount of energy needed to completely remove a unit volume of molecules from their neighbors to an infinite separation. The Hildebrand parameter can be used with nonpolar compounds, but it cannot be applied to complex chemistry in solutions.

Polarity can be separated to identify different contributions. For Example, the "Hansen's parameters" separate the cohesive energy density into dispersion, polar and hydrogen bonding contributions, as described in Hansen, C. M., "The Three Dimensional Solubility Parameter and Solvent Diffusion Coefficient", Doctoral Dissertation, The Technical University of Denmark, Danish Technical Press, Copenhagen, 1967, which is incorporated by reference.

The polarity, dipole moment, polarizability and hydrogen bonding ability of a solvent determines what type of compounds it is able to dissolve and with what other solvents or liquid compounds it is miscible. Generally, polar solvents will best dissolve other polar compounds. Similarly, non-polar solvents will best dissolve other non-polar compounds. Molecules that are highly polar like sugars, e.g., sucrose, or ionic compounds, such as inorganic salts, e.g., sodium chloride, generally dissolve only in very polar solvents like water. In contrast highly non-polar compounds like oils or waxes will generally dissolve only in very non-polar organic solvents such as hexane. It follows that water (polar) and hexane (non-polar) are not miscible with each other and will quickly separate into two layers or phases even after being vigorously shaken or agitated.

Traditional solvents used in industrial aromatic extraction processes include glycols: di-, tri- and tetraethyleneglycols, (DEG, TEG and TETRA, respectively); amides: N-methyl-pyrrolidone (NMP), N-formylmorpholine (NFM); or oxygenated derivatives of sulfur-bearing molecules such as dimethylsulfoxide (DMSO) or tetramethylenesulfone (sulfolane). These compounds have the general properties of industrial solvents, including thermal and chemical stability, low toxicity and corrosivity, ready availability and moderate cost.

It would be highly desirable to provide a solvent composition that has the desirable properties and characteristics of known industrial solvents that can be derived from a low value source that otherwise has limited utility and whose use or disposal may require installation of environmental safe guards, thereby incurring additional costs that must be bet by the refiner.

SUMMARY OF THE INVENTION

In accordance with the present disclosure, new solvent compositions have been identified that comprise a mixture of oxidized disulfide oils (ODSOs).

By-product disulfide oil (DSO) compounds derived from the mercaptan oxidative process of a refinery feedstock that have been oxidized have been found to constitute an abundant source of the ODSO compounds that are sulfoxides, sulfonates and sulfones. The recognition of the solvent properties of ODSO compounds derived from the oxidation of the DSO by-products of the mercaptan oxidation employed to reduce or eliminate sulfur compounds from refinery feedstocks transforms the low value by-product disulfide oils into a valuable industrial commodity that has utility and applicability in a broad range of fields.

As used herein, the abbreviations of oxidized disulfide oils ("ODSO") and disulfide oils ("DSO") will be understood to refer to the singular and plural forms, which may also appear as "DSO compounds" and "ODSO compounds", and each form may be used interchangeably.

On a global basis, mercaptan oxidation process units, often referred to as MEROX units, are commonly found in refineries and the significant volume of disulfide oils generated may be blended in low proportions with fuel oil, or processed in hydrotreating or hydrocracking process units, or even injected into the ground for disposal. When the disulfides are added to fuel oil, they are typically burned to produce steam or provide other utilities where they are produced. This use can raise environmental concerns where the combustion gases with sulfur-containing constituents are emitted in the refinery. The disulfide oils can undergo hydroprocessing, but hydroprocessing is not a favored method for disposal of waste oil because additional hydrogen is required and consumed in the process.

Table 1 includes examples of ODSO compounds produced by the oxidation of DSO by-product compounds produced in the MEROX sulfur reduction or sweetening process of hydrocarbons containing mercaptans. It will be understood that since the source of the DSO is a refinery feedstream, the R substituents vary, e.g., methyl and ethyl subgroups, and the number of sulfur atoms, S, in the as-received feedstream can extend to 3, i.e., trisulfide compounds. Analyses indicate that any trisulfides present are in trace quantities.

TABLE 1

| ODSO Name | Formula | Structure Examples |
| --- | --- | --- |
| Dialkyl-thiosulfoxide or alkyl-alkane-sulfinothioate | (R—SO—S—R) | S-Methyl methanesulfinothioate |
| Dialkyl-thiosulfones or Alkyl-Alkane-thiosulfonate | (R—SOO—S—R) | Methyl Methanethiosulfonate |
| Dialkyl-sulfonesulfoxide Or 1,2-alkyl-alkyl-disulfane 1,1,2-trioxide | (R—SOO—SO—R) | 1,2-Dimethyldisulfane 1,1,2-trioxide |
| Dialkyl-disulfone Or 1,2 alkyl-alkyl-disulfane 1,1,2,2-tetraoxide | (R—SOO—SOO—R) | 1,2-Dimethyldisulfane 1,1,2,2-tetraoxide |

TABLE 1-continued

| ODSO Name | Formula | Structure Examples |
| --- | --- | --- |
| Dialkyl-disulfoxide | (R—SO—SO—R) | 1,2-Dimethyldisulfane 1,2-dioxide |
| Alkyl-sulfoxidesulfonate | (R—SO—SOO—OH) | Methylsulfanesulfonic acid oxide |
| Alkyl-sulfonesulfonate | (R—SOO—SOO—OH) | 1-Hydroxy-2-methyldisulfane 1,1,2,2-tetraoxide |
| Alkyl-sulfoxidesulfinate | (R—SO—SO—OH) | 1-Hydroxy-2-methyldisulfane 1,2-dioxide |
| Alkyl-sulfonesulfinate | (R—SOO—SO—OH) | Methylsulfanesulfinic acid dioxide |

Table 1 includes ODSO compounds that are polar and water-soluble, and also those that are non-polar and water insoluble. ODSO compounds that contain 1 and 2 oxygen atoms are non-polar and water insoluble. ODSO compounds that contain 3 or more oxygen atoms are water-soluble. The production of either polar or non-polar ODSO compounds is in part dependent on the reaction conditions during the oxidation process.

The ODSO compounds that contain 3 or more oxygen atoms are water soluble over all concentrations and are also oil soluble at relatively low concentrations in the range of from 0.1 ppmw to 10 ppmw.

The oxidized disulfide oils from the enhanced MEROX process are highly effective as solvents in applications such as aromatic solvent extraction and additives to improve the lubricity of transportation fuels. Water soluble ODSO compounds have been found to be highly selective at removing benzene when compared to traditional solvents, i.e., non-ODSO aromatic extraction solvents, such as sulfolane. The ODSO solvents can also be used in solvent deasphalting processes and for oil displacement.

The disulfide oils having the general formula RSSR produced in the MEROX process can be oxidized without a catalyst or in the presence of one or more catalysts to produce a mixture of oxidized disulfide oil (ODSO) compounds. If a catalyst is used in the oxidation of the disulfide oils having the general formula RSSR to produce the oxidized disulfide oil (ODSO) compounds, it can be a heterogeneous or homogeneous oxidation catalyst. The oxidation catalyst can be selected from one or more heterogeneous or homogeneous catalyst comprising metals from the IUPAC Group 4-12 of the Periodic Table, including Ti, V, Mn, Co, Fe, Cr, Cu, Zn, W and Mo. In certain embodiments, suitable homogeneous catalysts include molybdenum naphthanate, sodium tungstate, molybdenum hexacarbonyl, tungsten hexacarbonyl, sodium tungstate and vanadium pentaoxide. In certain embodiments, suitable heterogeneous catalysts include Ti, V, Mn, Co, Fe, Cr, W, Mo, and combinations thereof deposited on a support such as alumina, silica-alumina, silica, natural zeolites, synthetic zeolites, and combinations comprising one or more of the above supports. A preferred catalyst is sodium tungstate, $Na_2WO_4.2H_2O$. A suitable product is commercially available from, e.g., Sigma-Alrich Co. LLC.

The oxidation to produce the OSDO can be carried out in an oxidation reaction vessel operating at a pressure in the range from about 1 bar to about 30 bars, or from about 1 bar to about 10 bars, or from about 1 bar to about 3 bars. The oxidation to produce the OSDO can be carried out at a temperature in the range from about 20° C. to 300° C., about 20° C. to 150° C., about 45° C. to 90° C., about 20° C. to 90° C., about 45° C. to 300° C., or about 45° C. to 150° C.

The molar feed ratio of oxidizing agent-to-mono-sulfur can be in the range of from about 1:1 to about 100:1, about 1:1 to about 30:1, or about 1:1 to about 4:1.

The residence time in the reaction vessel can be in the range of from about 5 to 180 minutes, about 15 to 90 minutes, about 15 minutes to 30 minutes, about 5 to 90 minutes, about 5 to 30 minutes, or about 15 to 180 minutes.

The new solvent composition of the present disclosure comprises at least one of a primary oxidized disulfide oil (ODSO) compound, selected from the group consisting of (R—SO—S—R'), (R—SOO—S—R'), (R—SOO—SO—R'),
(R—SOO—SOO—R'), (R—SO—SO—R'), (R—SO—SOO—OH),
(R—SOO—SOO—OH), (R—SO—SO—OH), and (R—SOO—SO—OH), and mixtures thereof,
where R and R' are alkyl groups comprising 1-10 carbon atoms.

In some embodiments, the new solvent composition of the present disclosure further comprises at least one of a secondary oxidized disulfide oil (ODSO) compound, selected from the group consisting of
(R—SOO—SO—R'),
(R—SOO—SOO—R'), (R—SO—SOO—OH),
(R—SOO—SOO—OH), (R—SO—SO—OH), and (R—SOO—SO—OH), and mixtures thereof,
where R and R' are alkyl groups comprising 1-10 carbon atoms,
and wherein the at least one secondary ODSO compound is present at a concentration of at least 0.1 ppmw.

In the description that follows, the terms "ODSO solvent", "ODSO solvent mixture" "ODSO solvent composition" and "ODSO compound(s)" may be used interchangeably for convenience.

Sources of ODSO Compounds

It is known in the art that the presence of mercaptans in petroleum products are undesirable because of their unpleasant odor and corrosivity and also because they degrade the stability of end-product fuels. Processes in oil refineries and natural gas processing plants that remove mercaptans and/or hydrogen sulfide ($H_2S$) are commonly referred to as sweetening processes because they result in products which no longer have the sour, foul odors of mercaptans and hydrogen sulfide. The liquid hydrocarbon disulfides can remain in the sweetened end products; or they can be used as part of the petroleum refinery or natural gas processing plant fuel; or they can be subjected to further downstream processing.

The MEROX designation is derived from the mercaptan oxidation step of the process. The MEROX process is a proprietary catalytic mercaptan oxidation process widely used in petroleum refineries and natural gas processing plants to remove mercaptans contained in end-products such as LPG, propane, butanes, light naphtha, kerosene and jet fuel by converting them into liquid hydrocarbon disulfides. It is an integrated process comprising the mercaptan extraction step in which mercaptans react with an aqueous caustic solution in the presence of a catalyst to form an alkylthiolate with a base, which is then oxidized in a wet air oxidation step to produce disulfide oils and a regenerated caustic solution that is recycled to the extraction step. The alkaline environment required in some versions of the practice of the MEROX process is provided by an aqueous solution of sodium hydroxide (NaOH), a strong base, or in other versions of the process, by ammonia, which is a relatively weaker base than sodium hydroxide, but also volatile and must be handled with special care due to its irritant and toxicity properties.

The stepwise reaction schemes for the MEROX process beginning with the treatment of the mercaptan are as follows:

$$2RSH+2NaOH \rightarrow 2NaSR+2H_2O \quad (1)$$

In the above reaction, RSH is a mercaptan and R is an organic group such as a methyl, ethyl, propyl or other hydrocarbon group. For example, the ethyl mercaptan (ethanethiol) has the formula $C_2H_5SH$.

The catalyst used in some versions of the MEROX process is a water-soluble liquid and in other versions the catalyst is impregnated onto charcoal granules. The catalyst used in the MEROX process can be an organometallic compound.

The second step is referred to as regeneration and it involves heating and oxidizing the caustic solution leaving the extractor. The oxidation results in converting the extracted mercaptans in the form of alkali metal thio-alkanes to organic disulfides (RSSR). These disulfides are water-insoluble liquids that are separated and decanted from the aqueous caustic solution. The regeneration reaction scheme is as follows:

$$4NaSR+O_2+2H_2O \rightarrow 2RSSR+4NaOH \quad (2)$$

In reactions (1) and (2), R is methyl or a hydrocarbon chain that can be straight, branched or cyclic. The R chains can be saturated or unsaturated. In most petroleum and diesel fractions, mixtures of mercaptans will occur such that the R groups in the disulfide oil (RSSR) can be the same or different groups.

The liquid disulfides created by the conversion of the mercaptans do not have these undesirable characteristics and have been retained in the MEROX treated fuels or removed and used elsewhere in the petroleum refinery. The MEROX process is generally more economical than a catalytic hydrodesulfurization process and achieves much the same result for the mercaptans removal. Economic and practical drawbacks associated with hydrodesulfurization processes include additional dedicated facilities to which the disulfide compounds must be transferred, use of expensive and sensitive catalysts and the treatment and disposal of the by-product sulfur-containing compounds.

BRIEF DESCRIPTION OF THE DRAWINGS

The process for the production and utility of the compositions of this disclosure will be described in more detail below and with reference to the attached figures in which.

DETAILED DESCRIPTION OF THE INVENTION

Compositions comprising mixtures of compounds found to have utility for applications such as solvents and lubricity additives can advantageously be produced by the oxidation of a mixture of disulfide oil (DSO) compounds recovered as a low value by-product of the mercaptan oxidation of a hydrocarbon feedstock.

The oxidation reaction can be conducted in any suitable reaction vessel. Examples of suitable vessels include, but are not limited to, one or more fixed-bed reactors, ebullated bed reactors, slurry bed reactors, moving bed reactors, continuous stirred tank reactor, and tubular reactors. In embodiments were a fixed bed is used, the reactor can also comprise a plurality of catalyst beds.

The oxidation reaction can be conducted in batch mode or continuously. The oxidation reaction is an exothermic reaction that raises the temperature of the vessel. In certain embodiments, the oxidation can be carried out in a cooled reactor and/or coupled to a heat exchanger to control and maintain the reaction vessel and reactants at a predetermined temperature. If a heat exchanger is coupled to the system, the excess heat can be recovered for later use. It appears that reducing the temperature of the reaction mixture below a predetermined value, or range, adversely effects the reaction kinetics and the extent of the exothermic reaction and prevents the reaction from going to completion.

In view of the exothermic nature of the oxidation reaction, the oxidant, e.g., hydrogen peroxide, is added to DSO which is initially at room temperature. The temperature of the reaction mixture increases and in an embodiment is maintained at about 80° C. for one hour.

In certain embodiments, the ODSO solvent compounds contain one or more alkyl groups with carbon numbers in the range of from 1 to 10. In certain embodiments, the number of sulfur atoms in the ODSO compounds comprising the solvents are in the range of from 1 to 3. In certain embodiments, the number of oxygen atoms in the ODSO compounds is in the range of from 1 to 5. In a preferred embodiment, the number of carbon atoms in the mixture of ODSO compounds comprising the solvent is in the range of from 1 to 20.

The ODSO solvent compositions of the present disclosure can be soluble or insoluble in oil at the effective or working concentrations. The ODSO solvents produced can be soluble or insoluble in water at the effective or working concentrations, depending on the ratio of DSO-to-oxidant present in the oxidation reaction.

In accordance with the present disclosure, both water soluble and water insoluble ODSO solvents can be produced by controlling the molar ratio of the reactants. For example, an oxidation reaction carried out with a hydrogen peroxide oxidant at a molar ratio of oxidant-to-DSO compounds (calculated based upon mono-sulfur content) of 1.87 produces an ODSO solvent composition comprising 7% water insoluble ODSO compounds and 93% water soluble compounds. An oxidation reaction carried out at a molar ratio of oxidant-to-DSO compounds (calculated based upon mono-sulfur content) of 2.40 produces an ODSO solvent composition comprising 1% water insoluble ODSO compounds and 99% water soluble compounds. An oxidation reaction carried out at a molar ratio of oxidant-to-DSO compounds (calculated based upon mono-sulfur content) of 2.89 produces an ODSO solvent composition comprising substantially no detectable water insoluble ODSO compounds and 100% water soluble compounds.

In these embodiments, any water soluble compounds comprising the solvent will settle to the bottom and form a layer which can be separated from the water insoluble compounds. For example, in certain embodiments, a settler tank can be used in batch or continuous mode for separation. In certain embodiments, two- or three-phase water booth separators known in the art can be used. In general, as the amount of oxidant that is added increases, there is more conversion to the polar, water soluble ODSO solvent.

The ODSO solvent compositions have boiling points in the range of from about 20° C. to 650° C. Water soluble ODSO compounds produced according to the present description generally have boiling points in the range of from about 20° C. to 650° C., while water insoluble ODSO compounds produced according to the present description generally have boiling points in the range of from about 20° C. to 250° C. In certain embodiments, the ODSO compounds have a dielectric constant that is less than or equal to 100 at 0° C.

In general, due to the nature of the reaction for synthesizing the ODSO solvent compositions, even when the ODSO solvent composition is comprised essentially of water soluble ODSO compounds, trace levels of water insoluble ODSO compounds will also be present in the ODSO solvent composition. Similarly, when the ODSO solvent composition is comprised principally of water insoluble ODSO compounds, trace levels of water soluble ODSO compounds will also be present in the ODSO solvent composition. At present, based on experience and knowledge gained from working with the present reaction mechanisms, and tests and analyses conducted, the trace levels of either of the respective water insoluble or water soluble ODSO compounds present is in the range of from about 0.1 ppmw to 10 ppmw.

EXAMPLES

In the following examples, ODSO compounds were produced by the catalytic oxidation of samples of disulfide oil (DSO) compounds recovered as a by-product of the mercaptan oxidation of a hydrocarbon refinery feedstock. The feed used in the following examples was composed of 98 W % of C1 and C2 disulfide oils.

The oxidation of the DSO compounds was performed in batch mode under reflux at atmospheric pressure, i.e., at approximately 1.01 bar. The hydrogen peroxide oxidant was added at room temperature, i.e., approximately 23° C. and produced an exothermic reaction. The molar ratio of oxidant-to-DSO compounds (calculated based upon monosulfur content) was 2.40. After the addition of the oxidant was complete, the reaction vessel temperature was set to reflux at 80° C. for approximately one hour.

Two immiscible layers formed, one a dark red to brown layer, hereinafter referred to as Composition 1, and a light-yellow layer, hereinafter referred to as Composition 2. A separating funnel was used to separate and isolate each of the two layers.

The catalyst used in the examples described below was sodium tungstate.

Example 1

Figure 1:
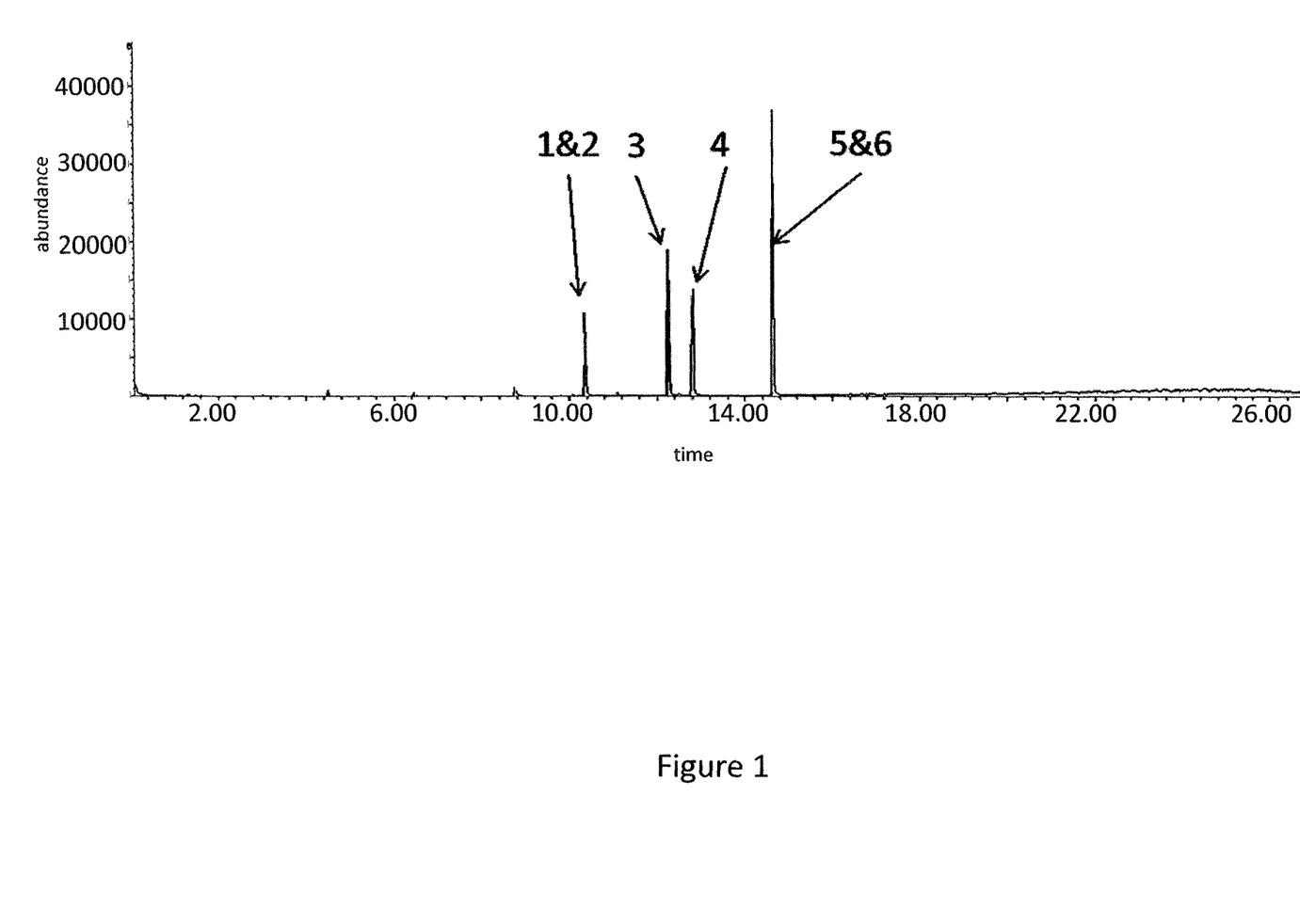
FIG. 1 is the experimental GC-MS chromatogram of the non-polar, water insoluble solvent composition, referred to below as Composition 1.

FIG. 1 depicts the experimental GC-MS chromatogram for a non-polar water insoluble ODSO solvent (Composition 1) of the present invention. The GC-MS spectra shows that the following compounds were present in the ODSO solvent of Composition 1:

Peak 1—methylmethanethiosulfonate ($H_3C$—SOO—S—$CH_3$);
Peak 2—dimethyldisulfoxide ($H_3C$—SO—SO—$CH_3$);
Peak 3—methylethanethiosulfonate ($H_3C$—SOO—S—$CH_2CH_3$);
Peak 4—ethylmethyldisulfoxide ($H_3C$—SO—SO—$CH_2CH_3$);
Peak 5—ethylethanethiosulfonate ($H_3CH_2C$—SOO—S—$CH_2CH_3$); and
Peak 6—diethyldisulfoxide ($H_3CH_2C$—SO—SO—$CH_2CH_3$).

Trace levels of ODSO compounds comprising 3+ oxygen atoms (not shown in the GC-MS data) are also present. It is clear from the GC-MS chromatogram shown in FIG. 1 that Composition 1 comprises a mixture of ODSO compounds that form the ODSO solvent composition.

Figure 2A:
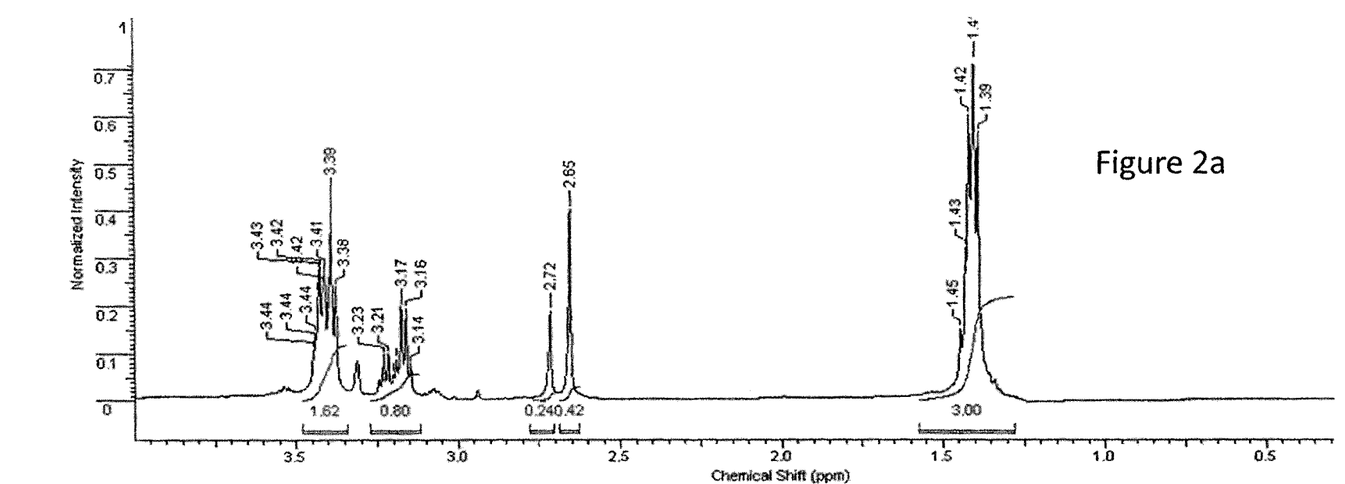
FIG. 2A is the experimental $^1$H-NMR spectrum of the non-polar, water insoluble solvent composition identified as Composition 1.

FIG. 2A is the experimental $^1$H-NMR spectrum for the non-polar water insoluble ODSO solvent (Composition 1).

Figure 2B:
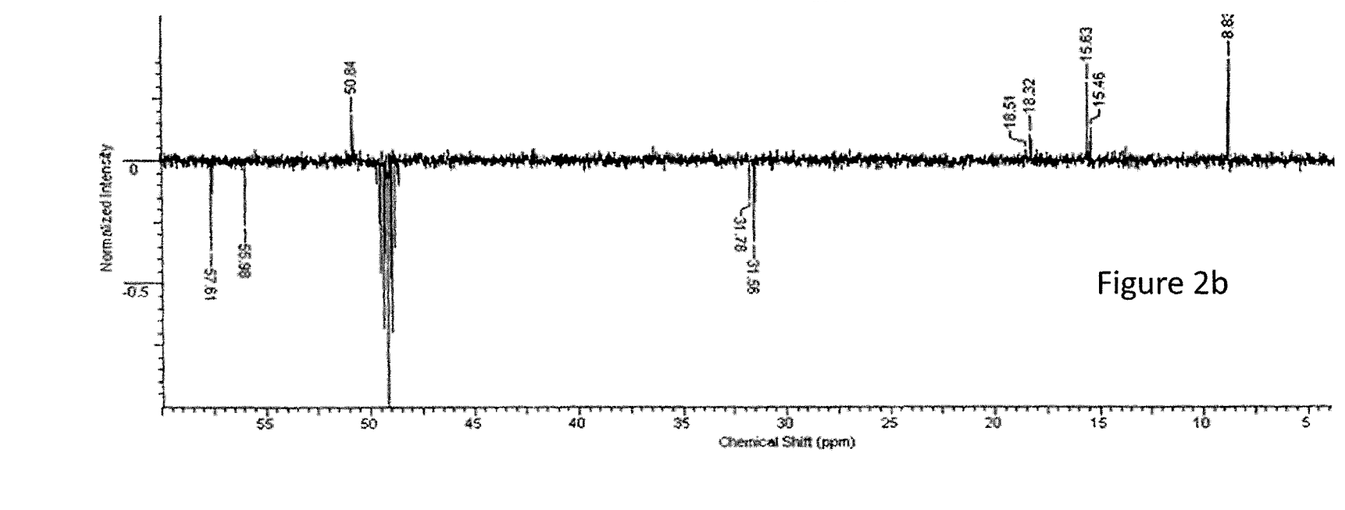
FIG. 2B is the experimental $^{13}$C-DEPT-135-NMR spectrum of the non-polar, water insoluble solvent composition identified as Composition 1.

FIG. 2B is the experimental (as distinguished from simulated) $^{13}$C-DEPT-135-NMR spectrum for Composition 1. Composition 1 was mixed with a $CD_3OD$ solvent and the spectrum was taken at 25° C. The DEPT (Distortionless Enhancement of Polarization Transfer) technique provides reliable information on attached protons in the sample efficiently and with high selectivity. The DEPT technique is a proton-carbon polarization transfer method and provides selective identification of methyl and/or methylene carbon atoms not available by other analytical techniques. In a DEPT-135 spectrum, $CH_3$ and CH signal peaks show positive intensities while $CH_2$ signal peaks are shown as negative intensities. In the spectrum in FIG. 2B, methyl carbons will have a positive intensity while methylene carbons exhibit a negative intensity. The peaks in the 48-50 ppm region belong to carbon signals of the $CD_3OD$ solvent.

In order to accurately identify spectral features in $^{13}$C-135-DEPT-NMR spectra, such as the one in FIG. 2b, and in order to categorize the corresponding ODSO compounds in the ODSO solvent compositions, $^{13}$C-NMR predictions (computational simulations) were carried out using ACD-Labs software for the following families of possible ODSO compounds:

dialkyl-thiosulfoxides (R—SO—S—R);
dialkyl-thiosulfones (R—SOO—S—R);
dialkyl-sulfonesulfoxide (R—SOO—SO—R);
dialkyl-disulfone (R—SOO—SOO—R);
dialkyl-disulfoxide (R—SO—SO—R);
alkyl-sulfoxidesulfonate (R—SO—SOO—OH);
alkyl-sulfonesulfonate (R—SOO—SOO—OH);
alkyl-sulfoxidesulfinate (R—SO—SO—OH);
alkyl-sulfonesulfinate (R—SOO—SO—OH);
alkyl-sulfoxidesulfenate (R—SO—S—OH);
alkyl-thiosulfonates (R—S—SOO—OH);
alkyl-thiosulfinates (R—S—SO—OH); and
esters (X—SO—OR or X—SOO—OR, where X=R—SO or R—SOO).

The $^{13}$C-NMR predictions for the families of possible OSDO compounds were saved in a database for comparison to experimental data. Since the DSO feed contained C1 and C2 hydrocarbons, predictions were carried out for ODSO solvents where R=C1 and C2 alkyls.

When comparing the experimental $^{13}$C-135-DEPT-NMR spectrum for Composition 1 (FIG. 2b) with the saved database of predicted spectra, it was found that the predicted dialkly-thiosulfone (R—SOO—S—R) spectrum mostly closely corresponded to the experimental spectrum. This suggests that dialkly-thiosulfones (R—SOO—S—R), where R=C1 and C2 alkyls, are major compounds in Composition 1. This result is complementary to the GC-MS data shown in FIG. 1. The predicted dialkly-thiosulfone (R—SOO—S—R) spectrum is shown in FIG. 3.

Figure 3:
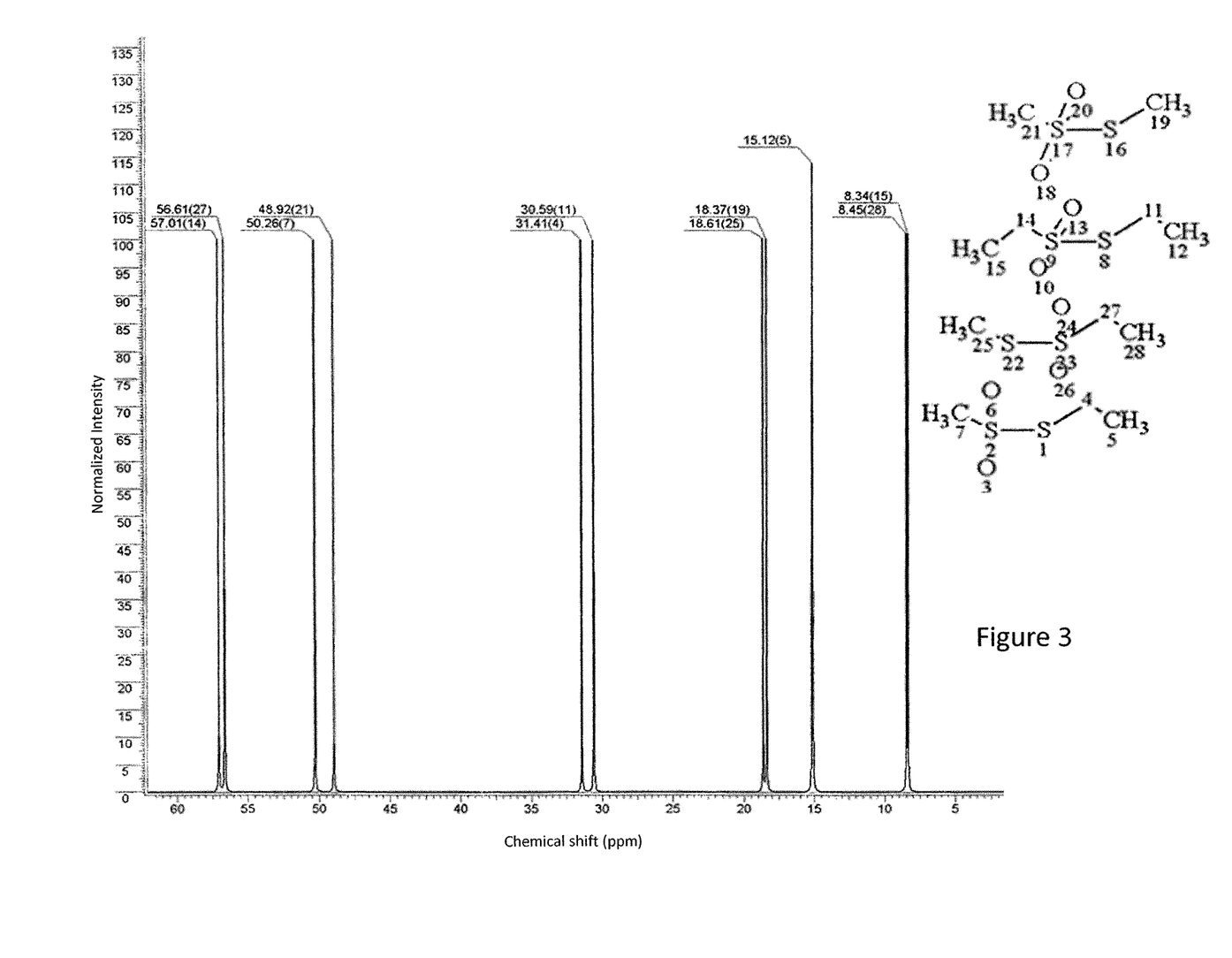
FIG. 3 is the simulated $^{13}$C-NMR spectrum of dialkyl-thiosulfones.

The simulated $^{13}$C-NMR spectrum in FIG. 3 for Composition 1 corresponds well with the experimental $^{13}$C-DEPT-135-NMR spectrum, suggesting the identified compound is present in Composition 1. It is clear from the NMR spectra shown in FIGS. 2a, 2b and 3 that Composition 1 comprises a mixture of ODSO compounds that form the ODSO solvent.

Example 2

Figure 4A:
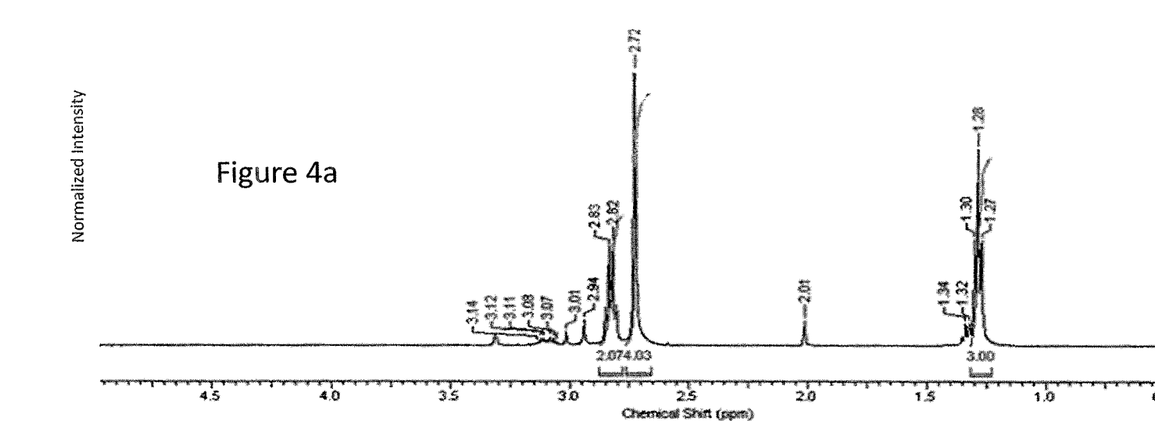
FIG. 4A is the experimental $^1$H-NMR spectrum of the polar, water soluble solvent composition, referred to below as Composition 2.

FIG. 4a is the experimental $^1$H-NMR spectrum for a polar water-soluble ODSO solvent composition identified as Composition 2.

Figure 4B:
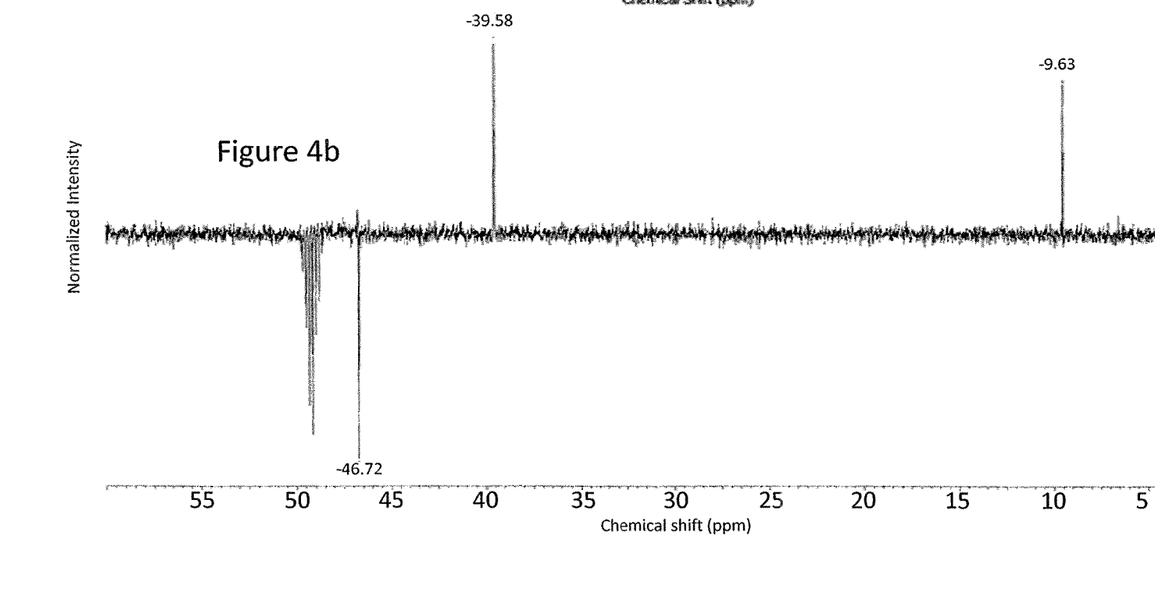
FIG. 4B is the experimental $^{13}$C-DEPT-135-NMR spectrum of the polar, water soluble solvent composition identified as Composition 2.

FIG. 4b is the experimental $^{13}$C-DEPT-135-NMR spectrum for Composition 2. Composition 2 was mixed with a $CD_3OD$ solvent and the spectrum was taken at 25° C. Similar to the peaks in FIG. 2b, in FIG. 4b methyl carbons have a positive intensity while methylene carbons exhibit a negative intensity. The peaks in the 48-50 ppm region belong to carbon signals of the $CD_3OD$ solvent.

Figure 5A:
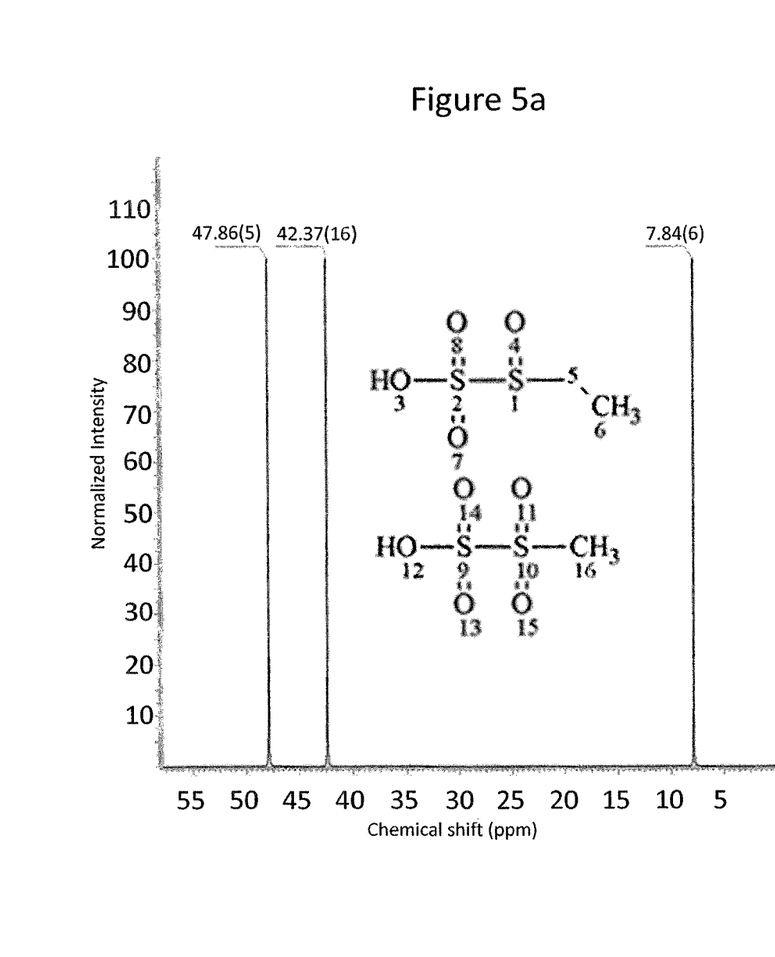
FIG. 5A is the simulated $^{13}$C-NMR spectrum of a combination of the alkyl-sulfoxidesulfonate (R—SO—SOO—OH) and alkyl-sulfonesulfonate (R—SOO—SOO—OH)

When comparing the experimental $^{13}$C-135-DEPT-NMR spectrum of FIG. 4b for Composition 2 with the saved database of predicted spectra, it was found that a combination of the predicted alkyl-sulfoxidesulfonate (R—SO—SOO—OH), alkyl-sulfonesulfonate (R—SOO—SOO—OH), alkyl-sulfoxidesulfinate (R—SO—SO—OH) and alkyl-sulfonesulfinate (R—SOO—SO—OH) most closely corresponded to the experimental spectrum. This suggests that alkyl-sulfoxidesulfonate (R—SO—SOO—OH), alkyl-sulfonesulfonate (R—SOO—SOO—OH), alkyl-sulfoxidesulfinate (R—SO—SO—OH) and alkyl-sulfonesulfinate (R—SOO—SO—OH) are major compounds in Composition 2. The combined predicted alkyl-sulfoxidesulfonate (R—SO—SOO—OH) and alkyl-sulfonesulfonate (R—SOO—SOO—OH) spectrum is shown in FIG. 5a. The combined predicted alkyl-sulfoxidesulfinate (R—SO—SO—OH) and alkyl-sulfonesulfinate (R—SOO—SO—OH) spectrum is shown in FIG. 5b.

Figure 5B:
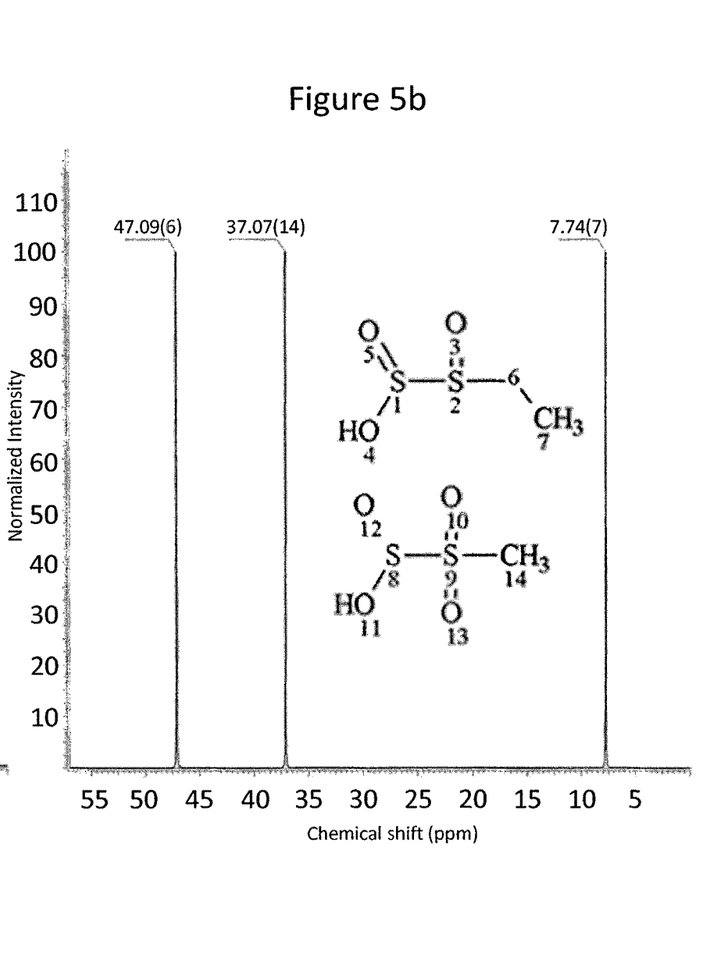
FIG. 5B is the simulated $^{13}$C-NMR spectrum of a combination of the alkyl-sulfoxidesulfinate (R—SO—SO—OH) and alkyl-sulfonesulfinate (R—SOO—SO—OH).

The simulated $^{13}$C-NMR spectrum in FIGS. 5a and 5b of Composition 2 corresponds well to the experimental $^{13}$C-DEPT-135-NMR spectrum, suggesting the identified compounds are present in Composition 2. It is clear from the NMR spectra shown in FIGS. 4a, 4b, 5a and 5b that Composition 2 comprises a mixture of ODSO compounds that form the ODSO solvent composition.

It is made clear by the results of the above analyses of Compositions 1 and 2 that ODSO compounds were present.

Example 3

In order to demonstrate its solvent effect, a comparative example of the use of the ODSO solvents of the present disclosure in an aromatic extraction process was conducted. An n-dodecane stock solution to which BTX was added was prepared for use as a feedstock for the extraction of aromatics using (1) a sulfolane solvent and (2) a water-soluble oxidized disulfide oil (ODSO) solvent. The number of carbon atoms in the individual water soluble OSDO compounds of the ODSO solvent used in this comparative example was in the range of from 2 to 4 carbon atoms. The prepared feedstock contained approximately 5 wt. % of benzene, 5 wt. % of toluene, 5 wt. % of o-xylene, 5 wt. % of m-xylene and 5 wt. % of p-xylene, as indicated in Table 2.

TABLE 2

| | Sulfolane Extraction (wt. %) | | | ODSO Extraction (wt. %) | | |
|---|---|---|---|---|---|---|
| | Stock | Extract | Normalized Selectivity | Stock | Extract | Normalized Selectivity |
| Benzene | 4.12 | 0.69 | 100 | 4.49 | 0.26 | 100 |
| Toluene | 4.4 | 0.37 | 50 | 4.95 | 0.02 | 7 |
| m-Xylene | 4.81 | 0.58 | 72 | 5.08 | 0 | 0 |
| p-Xylene | 4.67 | 0.21 | 27 | 4.95 | 0 | 0 |
| o-Xylene | 4.66 | 0.09 | 12 | 4.93 | 0.06 | 21 |

The feedstock and the respective solvents were added to separate flasks and vigorously shaken for 10 minutes at room temperature and atmospheric pressure. After mixing, in both cases two distinct phases separated and were isolated. The raffinate layer comprised the feedstock with a portion of its aromatics removed. The extract layer comprised the solvent with the portion of aromatics removed from the feedstock.

Table 2 indicates the results of a GC-MS analysis showing the wt. % of the BTX in the extract layer. When the selectivity is normalized to the benzene extracted, the data indicates that the sulfolane solvent extracts some of each of the other components in varying amounts. In contrast, the results in Table 2 indicate that the water soluble ODSO solvent has high selectivity for benzene, and significantly lower selectivity for toluene and o-xylene, with no measurable removal of the m- and p-xylene from the prepared feedstock.

It is clear from Table 2 that in embodiments where the targeted aromatic compound is benzene, a preferred aromatic extraction solvent is one or a mixture of ODSO compounds used alone, i.e., without other types of solvents.

The compositions of the present invention and method for their preparation have been described above and characterized in the attached figures; however, process modifications and variations will be apparent to those of ordinary skill in the art and the scope of protection for the invention is to be defined by the claims that follow.

We claim:

1. An oxidized disulfide oil (ODSO) mixture consisting of two or more primary oxidized disulfide oil (ODSO) compounds selected from the group consisting of
(R—SO—S—R'), (R—SOO—S—R'), (R—SOO—SO—R'),
(R—SOO—SOO—R'), (R—SO—SO—R'), (R—SO—SOO—OH),
(R—SOO—SOO—OH), (R—SO—SO—OH), and (R—SOO—SO—OH), and mixtures thereof,
where R and R' are alkyl groups each of which comprises from 1-10 carbon atoms,
and wherein the ODSO compounds in the mixture correspond to oxidized disulfide oils present in an effluent refinery hydrocarbon stream recovered following the catalytic oxidation of mercaptans present in the hydrocarbon stream.

2. The ODSO mixture of claim 1, wherein the mixture comprises water soluble and water insoluble compounds.

3. The ODSO mixture of claim 1, wherein the mixture has a dielectric constant that is less than or equal to 100 at 0° C.

4. The ODSO mixture of claim 1, wherein the number of oxygen atoms in the two or more primary ODSO compound is in the range of from 1 to 5.

5. The ODSO mixture of claim 1, wherein the disulfide oils are oxidized in the presence of a catalyst.

6. The ODSO mixture of claim 5, wherein the oxidized disulfide oils are formed in the presence of one or more heterogeneous or homogeneous catalysts comprising a metal from IUPAC Groups 4-12 of the Periodic Table.

7. The ODSO mixture of claim 1, wherein the catalyst is sodium tungstate.

8. The ODSO mixture of claim 4, wherein the oxidation of the disulfide oils is carried out in an oxidation vessel selected from one or more of the group consisting of a fixed-bed reactor, an ebullated bed reactor, a slurry bed reactor, a moving bed reactor, a continuous stirred tank reactor, and a tubular reactor.

9. The ODSO mixture of claim 1, wherein the oxidized disulfide oils are formed at a pressure in the range of from about 1 bar to 30 bars.

10. The ODSO mixture of claim 1, wherein the oxidized disulfide oils are formed at a temperature in the range of from about 20° C. to 300° C.

11. The ODSO mixture of claim 1, wherein the oxidized disulfide oils are formed at a molar feed ratio of oxidizing agent-to-mono-sulfur compounds in the range of from about 1:1 to about 100:1.

12. The ODSO mixture of claim 1, wherein the oxidized disulfide oils are formed a residence time of about 5 to 180 minutes.

13. The ODSO mixture of claim 1, that consists of:
methylmethanethiosulfonate (H$_3$C—SOO—S—CH$_3$);
dimethyldisulfoxide (H$_3$C—SO—SO—CH$_3$);
methylethanethiosulfonate (H$_3$C—SOO—S—CH$_2$CH$_3$);
ethylmethyldisulfoxide (H$_3$C—SO—SO—CH$_2$CH$_3$);

ethylethanethiosulfonate (H$_3$CH$_2$C—SOO—S—CH$_2$CH$_3$); and diethyldisulfoxide (H$_3$CH$_2$C—SO—SO—CH$_2$CH$_3$).

14. An oxidized disulfide oil (ODSO) mixture consisting of the following oxidized disulfide oil (ODSO) compounds:
(R—SO—S—R'), (R—SOO—S—R'), (R—SOO—SO—R'),
(R—SOO—SOO—R'), (R—SO—SO—R'), (R—SO—SOO—OH),
(R—SOO—SOO—OH), (R—SO—SO—OH), and (R—SOO—SO—OH),
  where R and R' are alkyl groups each of which comprises from 1-10 carbon atoms,
  and wherein the ODSO compounds in the mixture correspond to oxidized disulfide oils present in an effluent refinery hydrocarbon stream recovered following the catalytic oxidation of mercaptans present in the hydrocarbon stream.

* * * * *